US011918293B2

United States Patent
Grady et al.

(10) Patent No.: US 11,918,293 B2
(45) Date of Patent: Mar. 5, 2024

(54) SYSTEMS AND METHODS FOR ASSESSING ORGAN AND/OR TISSUE TRANSPLANTATION BY SIMULATING ONE OR MORE TRANSPLANT CHARACTERISTICS

(71) Applicant: HeartFlow, Inc., Redwood City, CA (US)

(72) Inventors: Leo Grady, Redwood City, CA (US); Charles A. Taylor, Redwood City, CA (US); Christopher Zarins, Redwood City, CA (US)

(73) Assignee: HeartFlow, Inc., Mountain View, CA (US)

( * ) Notice: Subject to any disclaimer, the term of this patent is extended or adjusted under 35 U.S.C. 154(b) by 289 days.

(21) Appl. No.: 17/106,987

(22) Filed: Nov. 30, 2020

(65) Prior Publication Data

US 2021/0093384 A1    Apr. 1, 2021

Related U.S. Application Data

(63) Continuation of application No. 16/680,005, filed on Nov. 11, 2019, now Pat. No. 10,881,465, which is a (Continued)

(51) Int. Cl.
*A61B 34/10* (2016.01)
*A61B 5/026* (2006.01)
(Continued)

(52) U.S. Cl.
CPC .......... *A61B 34/10* (2016.02); *A61B 5/0263* (2013.01); *A61B 6/032* (2013.01); *A61B 6/503* (2013.01);
(Continued)

(58) Field of Classification Search
CPC ....... A61B 34/10; A61B 5/0263; A61B 6/032; A61B 6/503; A61B 6/504; A61B 8/06;
(Continued)

(56) References Cited

U.S. PATENT DOCUMENTS 8,548,778 B1    10/2013  Hart et al.
10,470,730 B2 *  11/2019  Benishti ................. G16H 50/50
(Continued)

FOREIGN PATENT DOCUMENTS

CA    2 679 597      6/2008
JP    2013-146422    8/2013
(Continued)

OTHER PUBLICATIONS

Garcia-Valdecasas, Juan C., et al. "Changes in portal vein flow after adult living-donor liver transplantation: does it influence postoperative liver function ?. " Liver transplantation 9.6 (2003): 564-569. (Year: 2003).*

(Continued)

*Primary Examiner* — Michael Edward Cocchi
(74) *Attorney, Agent, or Firm* — Bookoff McAndrews, PLLC

(57) ABSTRACT

Systems and methods are disclosed for assessing organ and/or tissue transplantation by estimating blood flow through a virtual transplant model by receiving a patient-specific anatomical model of the intended transplant recipient; receiving a patient-specific anatomical model of the intended transplant donor, the model including the vasculature of the organ or tissue that is intended to be transplanted to the recipient; constructing a unified model of the connected system post transplantation, the connected system including the transplanted organ or tissue from the intended transplant donor and the vascular system of the intended transplant recipient; receiving one or more blood flow
(Continued)

characteristics of the connected system; assessing the suitability for an actual organ or tissue transplantation using the received blood flow characteristics; and outputting the assessment into an electronic storage medium or display.

20 Claims, 7 Drawing Sheets

Related U.S. Application Data continuation of application No. 15/357,008, filed on Nov. 21, 2016, now Pat. No. 10,499,990.

(60) Provisional application No. 62/258,930, filed on Nov. 23, 2015.

(51) Int. Cl.
| | | |
|---|---|---|
| *A61B 6/00* | (2006.01) | |
| *A61B 6/03* | (2006.01) | |
| *A61B 8/06* | (2006.01) | |
| *G06F 30/20* | (2020.01) | |
| *G06T 7/00* | (2017.01) | |
| *G06T 7/11* | (2017.01) | |
| *G09B 9/00* | (2006.01) | |
| *G09B 23/30* | (2006.01) | |
| *G16H 50/50* | (2018.01) | |

(52) U.S. Cl.
CPC ............... *A61B 6/504* (2013.01); *A61B 8/06* (2013.01); *G06F 30/20* (2020.01); *G06T 7/0012* (2013.01); *G06T 7/11* (2017.01); *G09B 9/00* (2013.01); *G09B 23/303* (2013.01); *G16H 50/50* (2018.01); *A61B 2034/104* (2016.02); *A61B 2034/105* (2016.02); *G06T 2207/10081* (2013.01); *G06T 2207/10088* (2013.01); *G06T 2207/10132* (2013.01); *G06T 2207/30048* (2013.01); *G06T 2207/30056* (2013.01); *G06T 2207/30084* (2013.01); *G06T 2207/30104* (2013.01); *G06T 2211/404* (2013.01)

(58) Field of Classification Search
CPC ........ A61B 2034/104; A61B 2034/105; G06F 30/20; G06F 30/25; G06F 30/27; G06F 30/28; G06T 7/0012; G06T 7/11; G06T 2207/10081; G06T 2207/10088; G06T 2207/10132; G06T 2207/30048; G06T 2207/30056; G06T 2207/30084; G06T 2207/30104; G06T 2211/404; G09B 9/00; G09B 23/303; G16H 50/50; G01F 1/66; G01F 1/72; H04L 67/131

See application file for complete search history.

(56) References Cited

U.S. PATENT DOCUMENTS

| | | |
|---|---|---|
| 2008/0132781 A1 | 6/2008 | Redel |
| 2010/0130878 A1 | 5/2010 | Lasso |
| 2010/0241404 A1 | 9/2010 | Taylor |
| 2012/0041318 A1* | 2/2012 | Taylor ............... A61B 34/10 600/504 |
| 2012/0122382 A1 | 5/2012 | Hoglund |
| 2012/0130878 A1 | 5/2012 | Moyse |
| 2013/0006067 A1 | 1/2013 | Foucher et al. |
| 2014/0045167 A1* | 2/2014 | Anderson ............. G16H 10/40 435/1.2 |
| 2014/0122382 A1* | 5/2014 | Elster ................. G16H 10/60 706/12 |
| 2014/0379318 A1 | 12/2014 | Spilker et al. |
| 2017/0000564 A1 | 1/2017 | Gordon et al. |

FOREIGN PATENT DOCUMENTS

| | | | | |
|---|---|---|---|---|
| JP | 2013-165844 | | 8/2013 | |
| JP | 2016533815 A | * | 8/2014 | ............ G16H 50/50 |
| JP | 2014-534889 | | 12/2014 | |
| JP | 2015-531264 | | 11/2015 | |
| WO | WO 2014/152753 | | 9/2014 | |

OTHER PUBLICATIONS

Oztekin, Asil, Dursun Delen, and Zhenyu James Kong. "Predicting the graft survival for heart-lung transplantation patients: an integrated data mining methodology." International journal of medical informatics 78.12 (2009): e84-e96. (Year: 2009).*

International Search Report and the Written Opinion issued in related PCT/US16/063027 dated Feb. 17, 2017 (11 pages).

Garcia-Valdecasas JC, Fuster J, Charco R, Bombuy E, Fondevila C, Ferrer J, et al. Changes in portal vein flow after adult living-donor liver transplantation: does it influence postoperative liver function? Liver Transplantation vol. 9, No. 6 (June), 2003: pp. 564-569 (Year: 2003).

* cited by examiner

SYSTEMS AND METHODS FOR ASSESSING ORGAN AND/OR TISSUE TRANSPLANTATION BY SIMULATING ONE OR MORE TRANSPLANT CHARACTERISTICS

RELATED APPLICATION(S)

This application is a continuation of and claims the benefit of priority to U.S. patent application Ser. No. 16/680,005, filed Nov. 11, 2019, which is a continuation of U.S. patent application Ser. No. 15/357,008, filed Nov. 21, 2016, now U.S. Pat. No. 10,499,990, which claims priority to U.S. Provisional Application No. 62/258,930 filed Nov. 23, 2016, all of which are incorporated herein by reference in their entireties.

FIELD OF THE DISCLOSURE

Various embodiments of the present disclosure relate generally to organ or tissue transplantation and related methods. More specifically, particular embodiments of the present disclosure relate to systems and methods for assessing organ or tissue transplantation.

BACKGROUND

Organ or tissue transplantation can be a life-saving procedure for a patient. However, the supply of viable organs may be severely limited and transplantation procedures may be unsuccessful. Some factors, including, but not limited to, a blood type of a recipient or donor, the health and severity of a recipient's organ failure, and the state of a donor organ, may cause a transplantation procedure to be unsuccessful and/or result in a sub-optimal donor match and/or outcome. In addition, for organ transplantation from a deceased donor to a living recipient, the length of time that a donor organ remains viable may be an important factor in matching a donor to a potential recipient. In addition, other factors that may cause unsuccessful transplantation procedures and/or result in a sub-optimal match may relate to whether, and to what degree, the size of a donor organ matches with the anatomic capacity and physiologic needs of a potential recipient. For example, one factor may include whether the cardiac output of a potential donor heart may meet the needs of a recipient patient. Another example of a factor that may cause an unsuccessful transplantation procedure and/or result in sub-optimal matching is whether, and to what degree, the expected renal blood flow and pressure and desired kidney function of a recipient matches the characteristics of a potential donor kidney. Similar considerations may arise for a potential liver or lung transplantation. Accordingly, there is a desire for a more effective tool to assist physicians in determining whether a transplantation procedure may be successful. Furthermore, there is a desire to improve the matching of a donated organ to the needs of a recipient or to improve the connecting of the blood supply of a recipient to the tissue, organ, and/or vasculature of a donor.

The foregoing general description and the following detailed description are exemplary and explanatory only and are not restrictive of the disclosure.

SUMMARY

According to certain aspects of the present disclosure, systems and methods are disclosed for assessing organ and/or tissue transplantation.

One method includes: receiving a patient-specific anatomical model of an intended transplant recipient, including a vasculature of the intended transplant recipient that is designated to supply blood to the transplanted organ or tissue; receiving a patient-specific anatomical model of an intended transplant donor, including a vasculature of the organ or tissue of the intended transplant donor that is designated to be transplanted to the intended transplant recipient; constructing a unified model of a connected system post transplantation, including at least some of the vasculature of the organ or tissue of the intended transplant donor and at least some of the vasculature of the intended transplant recipient designated to supply blood to the transplanted organ or tissue; estimating blood flow through the unified model of the connected system to compute one or more blood flow characteristics of the blood flow through the connected system; evaluating the planned transplantation using the computed blood flow characteristics; and outputting the evaluation into an electronic storage medium or display.

In accordance with another embodiment, a system for assessing organ and/or tissue transplantation by estimating blood flow through virtual transplant model comprises a data storage device storing instructions for assessing organ or tissue transplantation by estimating blood flow; and a processor configured to execute the instructions to perform a method including: receiving a patient-specific anatomical model of an intended transplant recipient, including a vasculature of the intended transplant recipient that is designated to supply blood to the transplanted organ or tissue; receiving a patient-specific anatomical model of an intended transplant donor, including a vasculature of the organ or tissue of the intended transplant donor that is designated to be transplanted to the intended transplant recipient; constructing a unified model of a connected system post transplantation, including at least some of the vasculature of the organ or tissue of the intended transplant donor and at least some of the vasculature of the intended transplant recipient designated to supply blood to the transplanted organ or tissue; estimating blood flow through the unified model of the connected system to compute one or more blood flow characteristics of the blood flow through the connected system; evaluating the planned transplantation using the computed blood flow characteristics; and outputting the evaluation into an electronic storage medium or display.

In accordance with another embodiment, a non-transitory computer readable medium for use on a computer system containing computer-executable programming instructions for performing a method of assessing organ and/or tissue transplantation by estimating blood flow through virtual transplant model, the method comprising: receiving a patient-specific anatomical model of an intended transplant recipient, including a vasculature of the intended transplant recipient that is designated to supply blood to the transplanted organ or tissue; receiving a patient-specific anatomical model of an intended transplant donor, including a vasculature of the organ or tissue of the intended transplant donor that is designated to be transplanted to the intended transplant recipient; constructing a unified model of a connected system post transplantation, including at least some of the vasculature of the organ or tissue of the intended transplant donor and at least some of the vasculature of the intended transplant recipient designated to supply blood to the transplanted organ or tissue; estimating blood flow through the unified model of the connected system to compute one or more blood flow characteristics of the blood flow through the connected system; evaluating the planned transplantation using the computed blood flow characteristics; and outputting the evaluation into an electronic storage medium or display.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments, and together with the description, serve to explain the principles of the disclosed embodiments.

Figure 1:
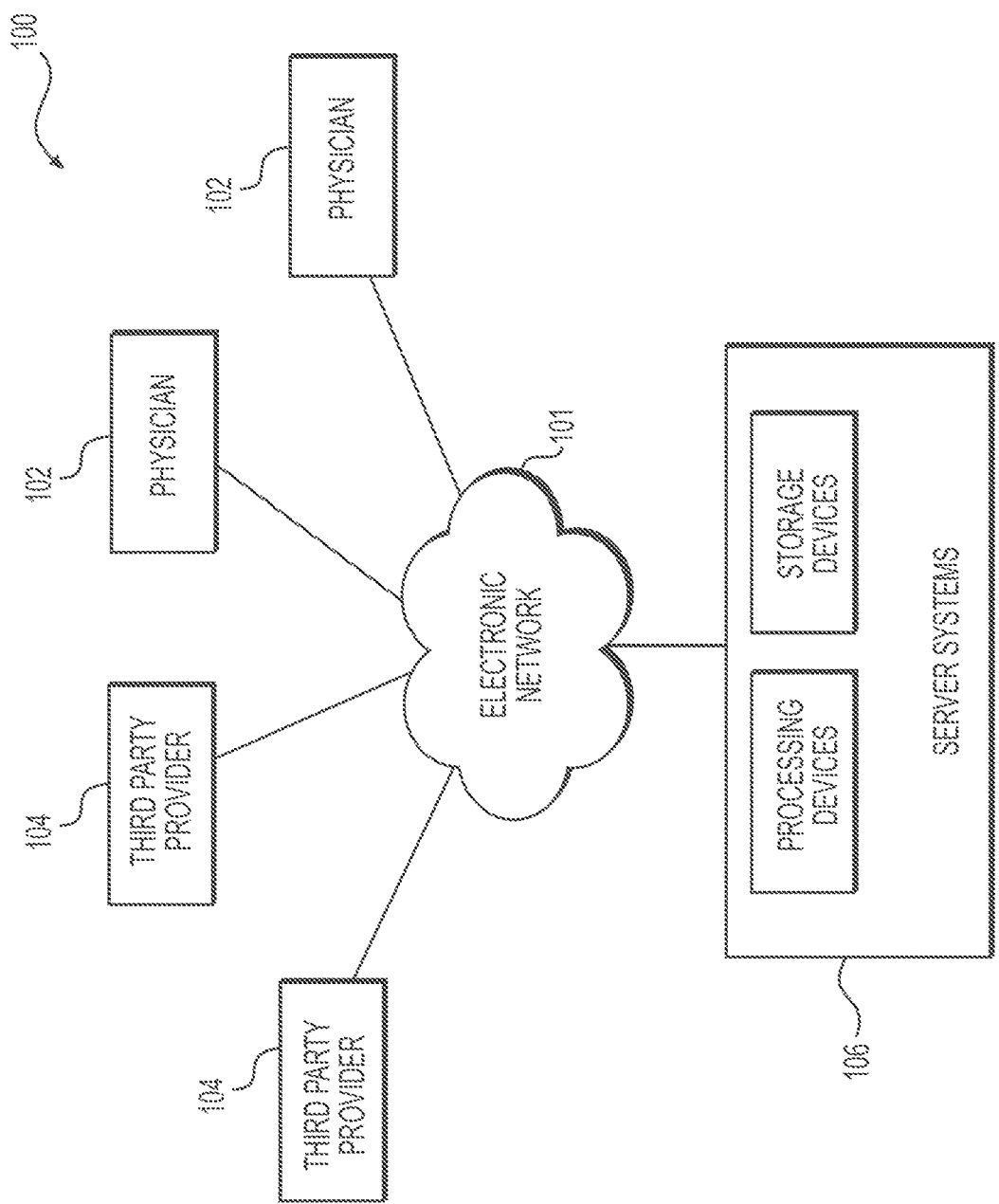
FIG. 1 depicts a block diagram of an exemplary system 100 and network for assessing organ and/or tissue transplantation by simulating, among other things, blood flow through a virtual transplant model, according to an exemplary embodiment.

The steps described in the methods may be performed in any order, or in conjunction with any other step. It is also contemplated that one or more of the steps may be omitted for performing the methods described in the present disclosure.

DESCRIPTION OF THE EMBODIMENTS

Reference will now be made in detail to the exemplary embodiments of the disclosure, examples of which are illustrated in the accompanying drawings. Wherever possible, the same reference numbers will be used throughout the drawings to refer to the same or like parts.

The systems and methods of the present disclosure include receiving a vascular and/or anatomical model of a donor and a recipient, performing a virtual transplantation by replacing the model of an organ or tissue of interest from the donor into the model of the recipient, computing transplant characteristics e.g., blood flow characteristics and organ-specific functional characteristics of the recipient system after the virtual transplant, and assessing the suitability and consequences for an actual organ or tissue transplantation using the computed characteristics, including, e.g., blood flow and/or functional characteristics of the connected system.

The embodiments of the present disclosure are directed to systems and methods for assisting a physician and/or medical personnel in determining whether an organ and/or tissue transplantation procedure may be successful. In some embodiments, the systems and methods of the disclosure may quantify or score the predicted success of a future transplantation procedure. In some embodiments, the systems and methods improve the matching between organ donors and recipients and/or assist in the optimization of surgical choices. The present disclosure includes a system and method for creating an anatomical model of the donor and recipient anatomy, virtually performing the transplantation by connecting the recipient and donor models, and then using computational techniques to calculate transplant characteristics (e.g., the adequacy of a blood supply characteristic in the donor organ and/or tissue, the functionality of the donor organ and/or tissue in the recipient, etc).

Additionally, the present disclosure provides systems and methods for assessing the impact of a transplantation procedure on the recipient's native tissues, organs, and/or vasculature. The impact assessment may also be used to calculate a score that estimates the likelihood of success for the procedure. The disclosed systems and methods may allow physicians to better optimize the chance of success for a procedure or determine that a donor organ and/or tissue would have a greater chance of success being transplanted to another patient. The embodiments of the present disclosure may include (i) segmenting a system vasculature of a recipient and a tissue or organ vasculature of a donor, (ii) performing a virtual transplantation, and (iii) simulating a post-transplant organ and system physiology for both a recipient and a donor (when living) to optimize the match for a recipient and minimize the consequences for a donor.

Referring now to the figures, FIG. 1 depicts a block diagram of an exemplary system 100 and network for assessing organ and/or tissue transplantation, according to an exemplary embodiment. Specifically, FIG. 1 depicts a plurality of physicians 102 and third party providers 104, any of whom may be connected to an electronic network 101, such as the Internet, through one or more computers, servers, and/or handheld mobile devices. Physicians 102 and/or third party providers 104 may create or otherwise obtain anatomical images of organ, tissue, and/or vasculature of the donor and/or recipient. Physicians 102 and/or third party providers 104 may also obtain any combination of patient-specific information. The patient-specific information may include, for example, age; medical history; blood type; the state of an organ, tissue, and/or vasculature; blood flow characteristics; blood supply demand characteristics; blood pressure; blood viscosity; patient activity or exercise level; time of death; etc. Physicians 102 and/or third party providers 104 may transmit the anatomical images and/or patient-specific information to server systems 106 over the electronic network 101. Server systems 106 may include storage devices for storing images and data received from physicians 102 and/or third party providers 104. Server systems 106 may also include processing devices for processing images and data stored in the storage devices.

Figure 2:
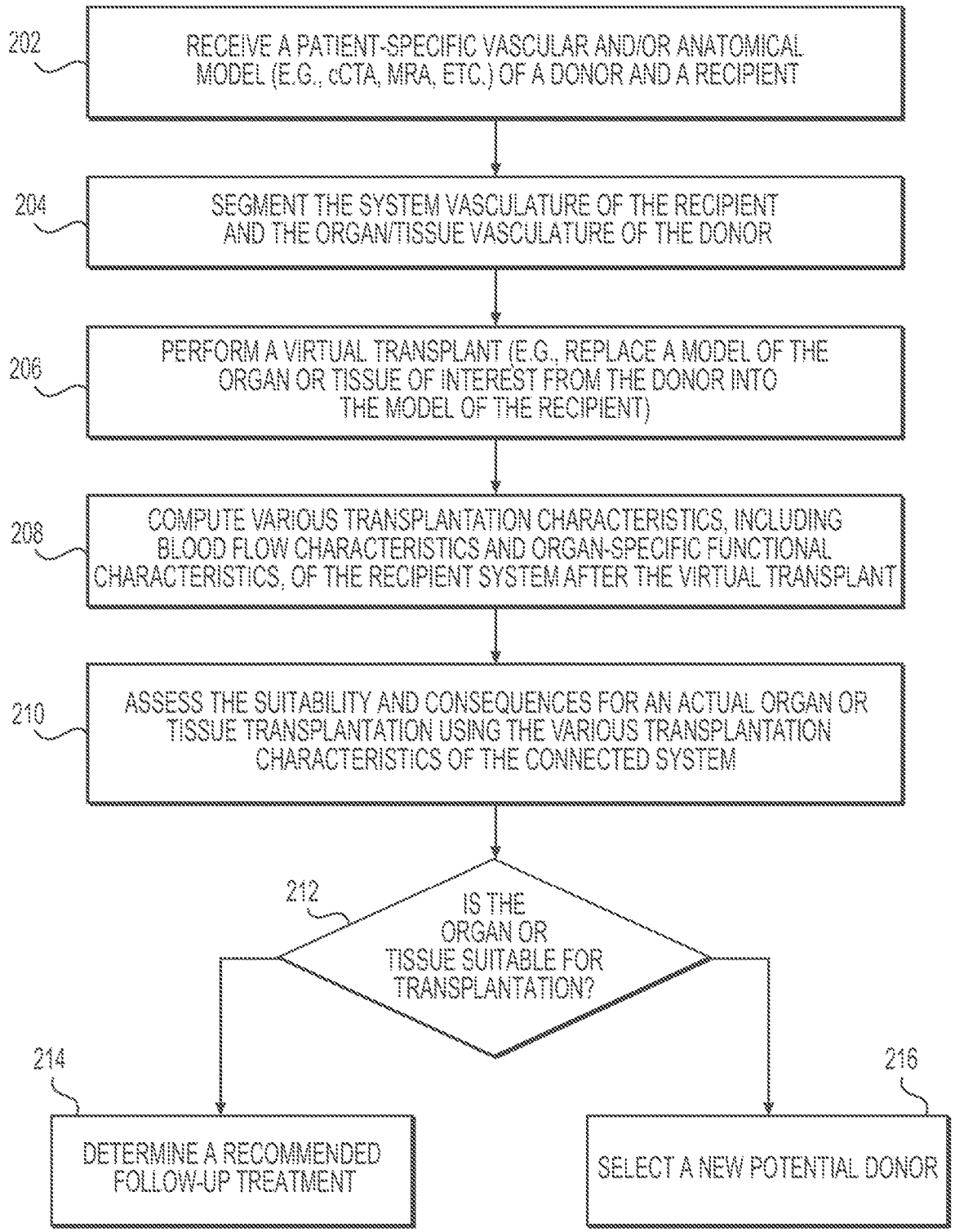
FIG. 2 is a block diagram of an exemplary method 200 of assessing organ and/or tissue transplantation by simulating, among other things, blood flow through a virtual transplant model, according to an exemplary embodiment of the present disclosure.

FIG. 2 is a block diagram of an exemplary method of assessing organ and/or tissue transplantation, according to an exemplary embodiment of the present disclosure. The method of FIG. 2 may be performed by server systems 106, based on information, images, and data received from physicians 102 and/or third party providers 104 over electronic network 101.

In one embodiment, step 202 may include receiving a patient-specific vascular and/or anatomical model of a transplant donor and a transplant recipient. This model may have been constructed by extracting a model from one or more medical images (e.g., a computerized tomography (CT), fractional flow reserve-computerized tomography (FFR-CT), magnetic resonance (MR), ultrasound, angiography, etc.). In another embodiment, one or more of the models may be constructed by using patient information to modify global parameters from a library of previously constructed virtual organs. The model may include a representation of a vascular system, subsystem, partial system, and/or anatomy for any intended transplant, including, for example, a heart transplant (e.g., coronaries, aorta, etc.), liver transplant (e.g., hepatic arteries, portal veins, etc.), lung transplant (e.g., pulmonary arteries), thymus transplant (e.g., internal thoracic artery, superior thyroid artery, inferior thyroids, etc.), kidney transplant (e.g., renal vessels, external iliac, etc.), intestine transplant (e.g., visceral vasculature), pancreas transplant (e.g., coeliac artery, superior mesenteric artery, splenic artery, greater pancreatic artery, superior pancreaticoduodenal artery, inferior pancreaticoduodenal artery, etc.), or transplant of a limb (e.g., ulnar artery, radial artery, etc. for the hand).

In one embodiment, step 204 may include segmenting the system vasculature of the recipient and the organ and/or tissue vasculature of the donor. The segmentation may allow the calculation of blood flow and/or blood supply demand characteristics, or the location of connection points for performing a virtual transplant. The segmentation of step 204 may occur according to the exemplary techniques described with respect to FIG. 4. In some embodiments, the model(s) received in step 202 may already be in segmented form, and step 204 may be unnecessary.

Step 206 may include performing a virtual transplant of the donor organ, tissue, and/or vasculature into the recipient system. For example, step 206 may include placing the model of the organ, tissue, and/or vasculature of interest from the donor into the model of the recipient. In one embodiment, performing a virtual transplant may comprise locating connection points between the segmented model of the recipient anatomy and the segmented model of the donor anatomy, and updating an electronic display of a single 3D model to reflect the post-transplantation organ, tissue, and/or vasculature. In one embodiment, a calculation of, e.g., blood flow characteristics and/or blood supply demand characteristics, in the patient-specific models of the recipient and donor anatomy may assist in locating the connection points. The final 3D model, reflecting the post-transplantation organ, tissue, vasculature, and/or system, may be stored in an electronic storage device (hard drive, network drive, cloud storage, portable disk, etc.).

Step 208 may include computing one or more various transplantation characteristics, including, e.g., blood flow characteristics and/or organ-specific functional characteristics of the recipient system after the virtual transplant. For purposes of this disclosure, blood flow characteristics may include, but are not limited to, blood pressure, fractional flow reserve, blood flow rate or flow velocity, and organ and/or tissue perfusion characteristics. Likewise, functional characteristics, which may be specific to the transplanted organ or tissue, may include, but are not limited to, cardiac output for the heart, glomerular filtration rate from the kidney, clearance capacity of the liver, and tissue perfusion for a transplanted tissue, within a connected system (e.g., the organ, tissue, and/or vasculature of the donor and recipient). A new blood flow or physiologic functional characteristic may be calculated by performing, with the connected vascular model, a 3D blood flow simulation, a reduced order model (e.g., 1D) blood flow simulation, an estimation using machine learning from a database, or a combination thereof. Step 208 may also include coupling the blood flow to an organ-specific physiologic parameter. In one embodiment, a blood flow simulation may include a generation of microcirculatory models and computing organ functions. Step 208 may further include outputting the determined blood flow and/or functional characteristics to an electronic display and/or an electronic storage device (e.g., hard drive, network drive, cloud storage, portable disk, etc.).

Step 210 may include assessing the suitability and consequences for an actual organ or tissue transplantation based on the virtual transplantation. In one embodiment, the assessment may include comparing the blood flow characteristics, blood supply demand characteristics, and/or functional characteristics received prior to, during, and/or post virtual transplantation. Step 210 may further comprise using the blood flow characteristics, blood supply demand characteristics, and/or functional characteristics to suggest, quantify, and/or score the likelihood of success for an actual organ/tissue transplantation.

Step 212 may include determining whether the intended transplant organ, tissue, and/or vasculature is suitable for transplantation, based on the assessment of step 210. If, subsequent to step 212, the intended transplant organ, tissue, and/or vasculature is indeed suitable for transplantation, then step 214 may include determining a recommended follow-up treatment. If, subsequent to step 212, the intended transplant organ, tissue, and/or vasculature is determined to be not suitable for transplantation, then step 216 may include selecting a new potential donor, and the steps of method 200 may be repeated.

Figure 3:
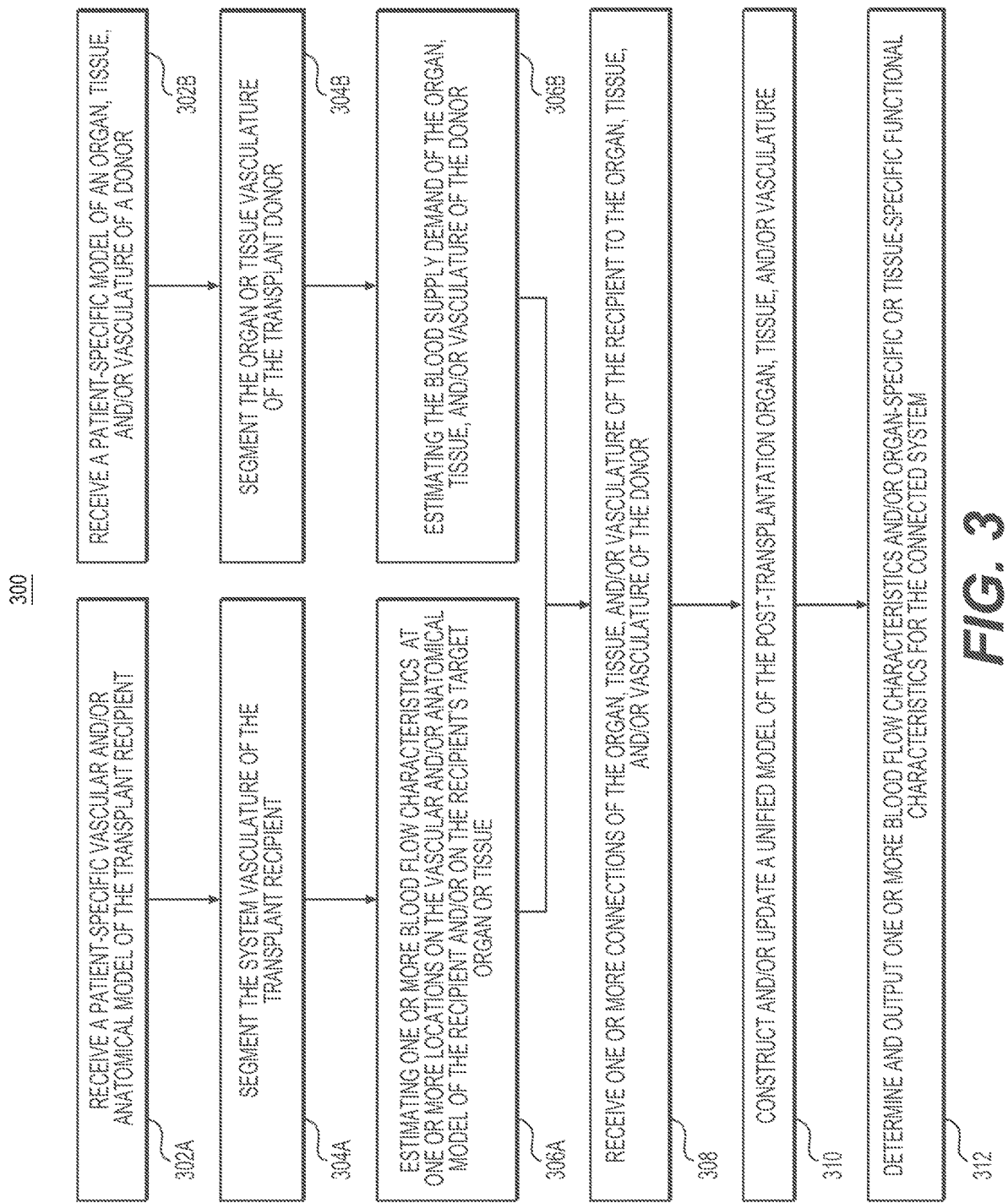
FIG. 3 is a block diagram of an exemplary method 300 of performing a virtual transplantation, according to an exemplary embodiment of the present disclosure.

FIG. 3 is a block diagram of an exemplary method 300 of performing a virtual transplantation, according to an exemplary embodiment of the present disclosure. Method 300 may be performed by server systems 106, based on information, images, and data received from physicians 102 and/or third party providers 104 over electronic network 101.

In one embodiment, step 302A may include receiving a patient-specific vascular and/or anatomical model of the intended transplant recipient. Likewise, step 302B may include receiving a patient-specific model of an organ, tissue, and/or vasculature of the intended transplant donor.

In one embodiment, one or more of the models may have been constructed by extracting a model from one or more medical images (e.g., a CT, MR, ultrasound, angiography, etc.) of the donor and/or recipient. In another embodiment, one or more of the models may be constructed by using patient information to modify global parameters from a library of previously constructed virtual organs. For example, one or more models may be constructed using an average model from a database of patients of a similar age, gender, weight, medical history, etc. The model(s) may include a representation of a vascular system, subsystem, partial system, and/or anatomy for any intended transplant, as explained above.

Step 304A may include segmenting the vasculature of the recipient's vascular system, comprising the organ or tissue to be replaced. Likewise, step 304B may include segmenting the vasculature of the intended transplant organ or tissue of the intended transplant donor. Steps 304A and 304B may comprise segmenting one or more images of the recipient or donor, respectively, into one or more voxels. A voxel may be an element of volume that may be used as a unit for segmentation. Step 304A may further include identifying the voxels belonging to a vasculature that provides circulation to the organ or tissue to be replaced, and then deriving a patient-specific model of a system vasculature of the transplant recipient from the identified voxels. Likewise, step 304B may further include identifying the voxels belonging to a vasculature of the organ or tissue to be transplanted, and then deriving a patient-specific model of the organ or tissue vasculature of the transplant donor from the identified voxels. Steps 304A and 304B may be performed by a processor of server system 106.

Step 306A may include estimating one or more blood flow characteristics (e.g., blood pressure, fractional flow reserve, flow rate or flow velocity, organ and/or tissue perfusion characteristics, etc.) at one or more locations on the vascular and/or anatomical model of the recipient and/or on the recipient's organ or tissue to be replaced. This information may be measured (invasively or noninvasively) or calculated (e.g., via a 3D fluid simulation, reduced order model fluid simulation, prediction from a database, etc.). In one embodiment, the blood flow characteristics may be determined by applying a trained machine learning algorithm (e.g., as in method 500 depicted in FIG. 5) based on a database of known blood flow characteristics from patient-specific parameters. In addition, the blood flow characteristics data may be registered and digitally overlaid on the patient-specific model of the system vasculature of the intended transplant recipient. Thus, the model may show blood flow characteristics for each area of the vascular network. In one embodiment, receiving information on blood flow characteristics may include segmenting the system vasculature of the recipient, and may further include receiving information on the blood flow characteristics of each segment.

Likewise, step 306B may include estimating the blood supply demand of the organ, tissue, and/or vasculature to be transplanted from the donor. This estimation may be performed by determining, e.g., a mass of the organ, tissue, and/or vasculature to be transplanted, and using an allometric relationship to estimate a blood supply demand. In such embodiments, the obtained donor organ model may be modified based on information relating to an actual donor patient. Such information may include, e.g., age, weight, or any other suitable patient information. In one embodiment, the blood supply demand may be estimated from pre-specified conditions where, for example, the donor organ model was obtained from a library of previously created virtual organs. In one embodiment, the estimation of the blood supply demand may include segmenting the organ vasculature of the donor. In one embodiment, the blood supply demand characteristics data may be registered and digitally overlaid on the patient-specific model of the organ, tissue, and/or vasculature of the intended transplant donor. Thus, the model may show blood supply demand characteristics for each area of the organ, tissue, and/or vasculature model.

In another embodiment, steps 306A and 306B may further or alternatively include estimating the blood supply demand of the vascular and/or anatomical model(s) of the recipient, and the blood flow characteristics of the organ, tissue, and/or vasculature of the donor.

In yet another embodiments, steps 306A and 306B may further or alternatively include estimating or receiving other characteristics of the vascular and/or anatomical model(s) of the recipient, and the organ, tissue, and/or vasculature of the donor, including, but not limited to, characteristics related to immunology, blood type, pathology, anatomy, and/or genetics.

Step 308 may include receiving one or more connections of the organ, tissue, and/or vasculature of the recipient to the organ, tissue, and/or vasculature of the donor. For example, where a recipient is targeted to receive a heart transplant from a donor, step 308 may include determining one or more connections between the heart of the donor and the vascular system of the recipient that would provide circulation to the transplanted heart. These connections may be received automatically (e.g., by using a standardized or automated connection) or interactively from a user (e.g., a cardiologist or imaging technician). In one embodiment, these connections may be modeled by creating a single 3D vascular model containing the organ, tissue, and/or vasculature of the recipient and the organ, tissue, and/or vasculature of the donor (e.g., by connecting the 3D surfaces of the two models and smoothing the connected surface mesh at the connection location). Alternately, for a reduced order model or machine learning driven model, the connections may be modeled by creating a unified representation of the connection without modifying a 3D surface.

Step 310 may include constructing and/or updating a single 3D model of the post-transplantation organ, tissue, and/or vasculature. For example, the original organ, tissue, and/or vasculature of the recipient may be removed from a recipient's model by closing the original recipient model distal to the one or more connections determined in step 308. The constructed and/or updated 3D model may be stored to an electronic storage device (e.g., hard drive, network drive, cloud storage, portable disk, etc.). In some embodiments, the step 310 may include determining the effects of the transplanted organ, tissue, and/or vasculature on neighboring organs, tissues, and/or vasculature of the recipient, and constructing and/or updating a unified model that reflects those effects.

Step 312 may include determining and outputting one or more transplantation characteristics, for the connected system represented by the single 3D model from step 310. The transplantation characteristics may include, but are not limited to, blood flow characteristics and functional characteristics of the connected system, as described above (e.g., as in step 208 of method 200). A new blood flow or physiologic functional characteristic may be calculated by performing, with the connected vascular model, a 3D blood flow simulation, a reduced order model (e.g., 1D) blood flow simulation, an estimation using machine learning from a database, or a combination thereof. Step 312 may also include coupling the blood flow to an organ-specific physiologic parameter. In one embodiment, a blood flow simulation may include a generation of microcirculatory models and computing organ functions. In one embodiment, the blood flow characteristics may be determined by applying a trained machine learning algorithm (e.g., as described relative to method 500 depicted in FIG. 5) based on a database of known blood flow characteristics from patient-specific parameters. Step 312 may include outputting the determined blood flow characteristic to an electronic display and/or an electronic storage device (e.g., hard drive, network drive, cloud storage, portable disk, etc.). In some embodiments, step 312 may further or alternatively include displaying and/or storing blood flow characteristics and/or organ-specific functional characteristics received prior to, during, and/or post virtual transplantation.

Figure 6:
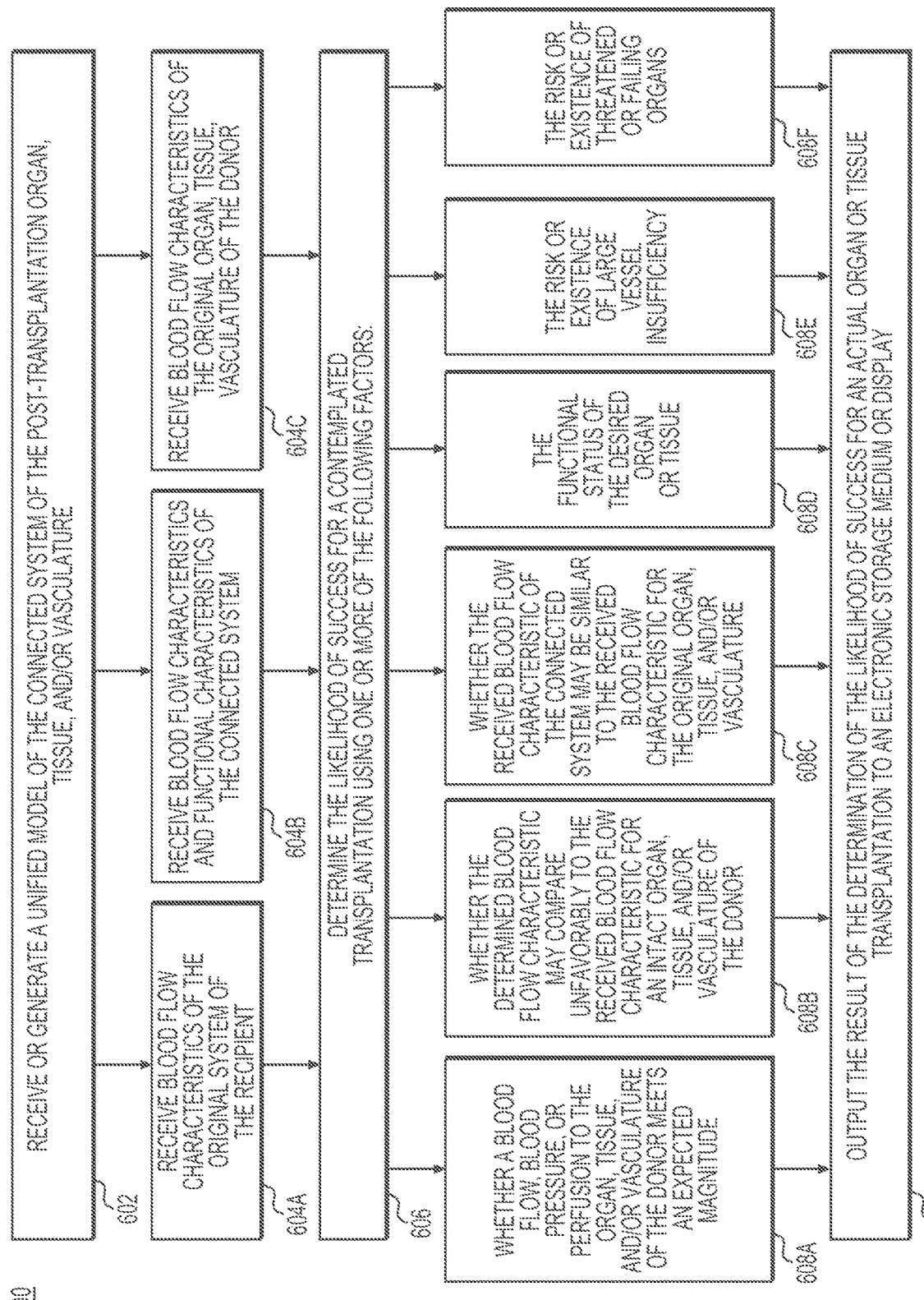
FIG. 6 is a block diagram of an exemplary method 600 of assessing the suitability and consequences for an actual organ or tissue transplantation using blood flow characteristics and/or organ-specific or tissue-specific functional characteristics of the connected system, according to an exemplary embodiment of the present disclosure.

Some embodiments may include, subsequent to performing the steps of method 300, using the transplantation characteristics (e.g., blood flow characteristics and/or organ-specific characteristics received after the virtual transplantation) to suggest, quantify, and/or score the likelihood of success for an actually contemplated organ and/or tissue transplantation (e.g., as described in method 600 depicted in FIG. 6).

Figure 4:
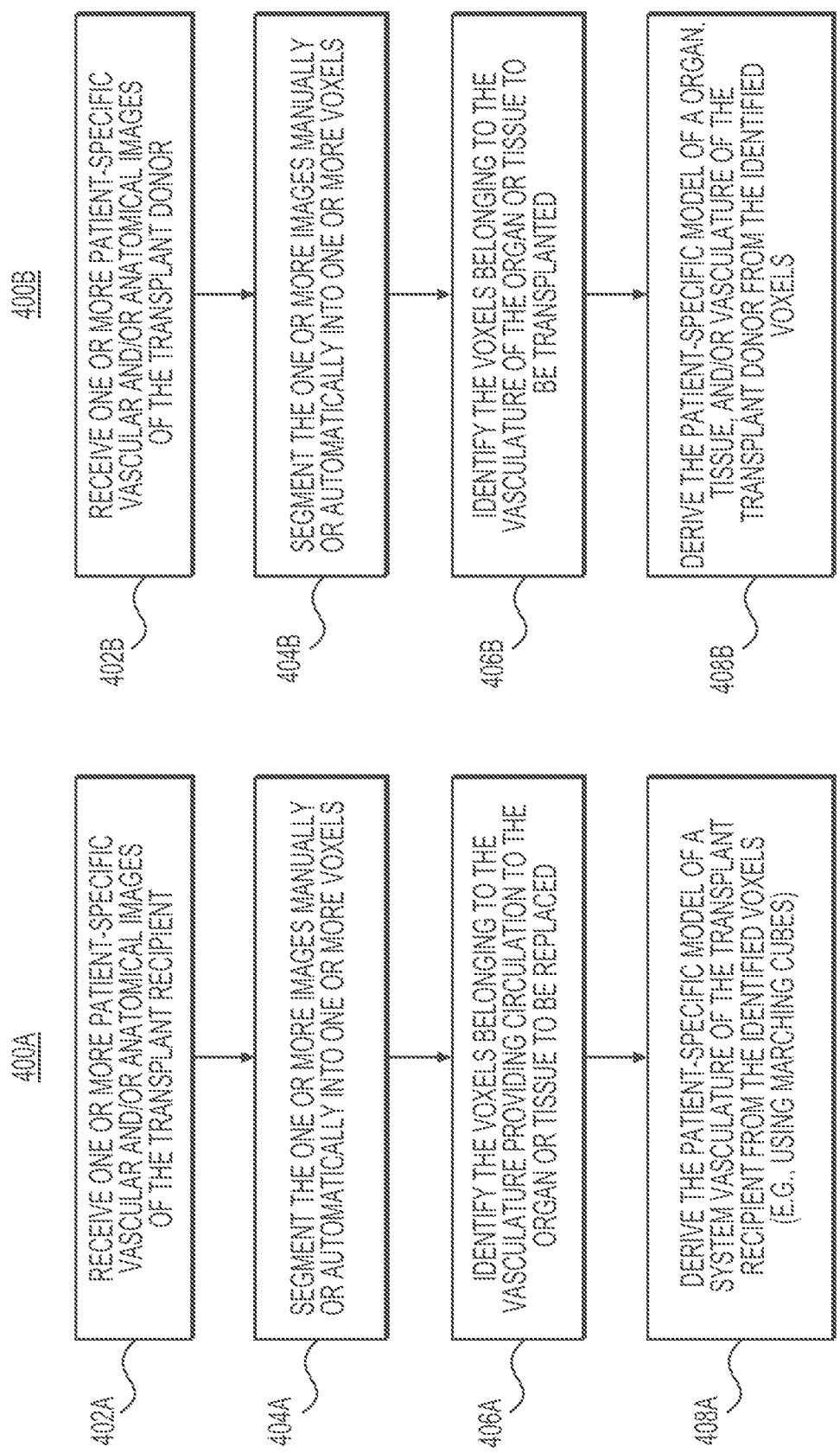
FIG. 4 is a block diagram of exemplary methods 400A and 400B of segmenting a system vasculature of the intended transplant recipient and of the organ or tissue vasculature of the intended transplant donor, respectively, according to an exemplary embodiment of the present disclosure.

FIG. 4 is a block diagram depicting exemplary methods 400A and 400B for segmenting a system vasculature of the intended transplant recipient and/or of the organ or tissue vasculature of the intended transplant donor, respectively, according to an exemplary embodiment of the present disclosure. Furthermore, methods 400A and 400B may be exemplary embodiments of performing step 204 of method 200. Alternatively or additionally, methods 400A and 400B may be exemplary embodiments of performing steps 302A and 302B, respectively, of method 300. Methods 400A and 400B may be performed by server systems 106, based on information, images, and data received from physicians 102 and/or third party providers 104 over electronic network 101.

Step 402A may include receiving one or more patient-specific vascular and/or anatomical images of the intended transplant recipient. Likewise, step 402B may include receiving one or more patient-specific vascular and/or anatomical images of the intended transplant donor. The images may be obtained from any one or more invasive or noninvasive scanning modalities, including, but not limited to, coronary computerized tomography angiography (cCTA), magnetic resonance (MR) imaging, positron emission tomography, etc. Steps 404A and 404B may include automatically segmenting the one or more received images into one or more voxels, using a computer processor.

Step 406A may include identifying the voxels belonging to the vasculature, of the intended transplant recipient, providing circulation to the organ or tissue to be replaced. Likewise, step 406B may include Identifying the voxels belonging to the vasculature of the organ or tissue to be transplanted from the intended transplant donor.

Step 408A may include deriving the patient-specific model of a system vasculature of the transplant recipient from the identified voxels. Likewise, step 408B may include deriving the patient-specific model of an organ, tissue, and/or vasculature of the transplant donor from the identified voxels. The segmentation, identification, and/or derivation processes in methods 400A and 400B may be performed automatically using a computer processor (e.g., by utilizing the marching cube algorithm). The marching cubes algorithm may be used to perform surface reconstruction from a set of identified voxels. In some embodiments, other surface reconstruction methods may be used. Additionally or alternately, segmentation may performed by an number of known algorithms, e.g., thresholding, adaptive thresholding, region growing, graph cuts, random walker, level sets, machine (deep) learning, active shapes, active surfaces, active appearance models, etc.

Figure 5:
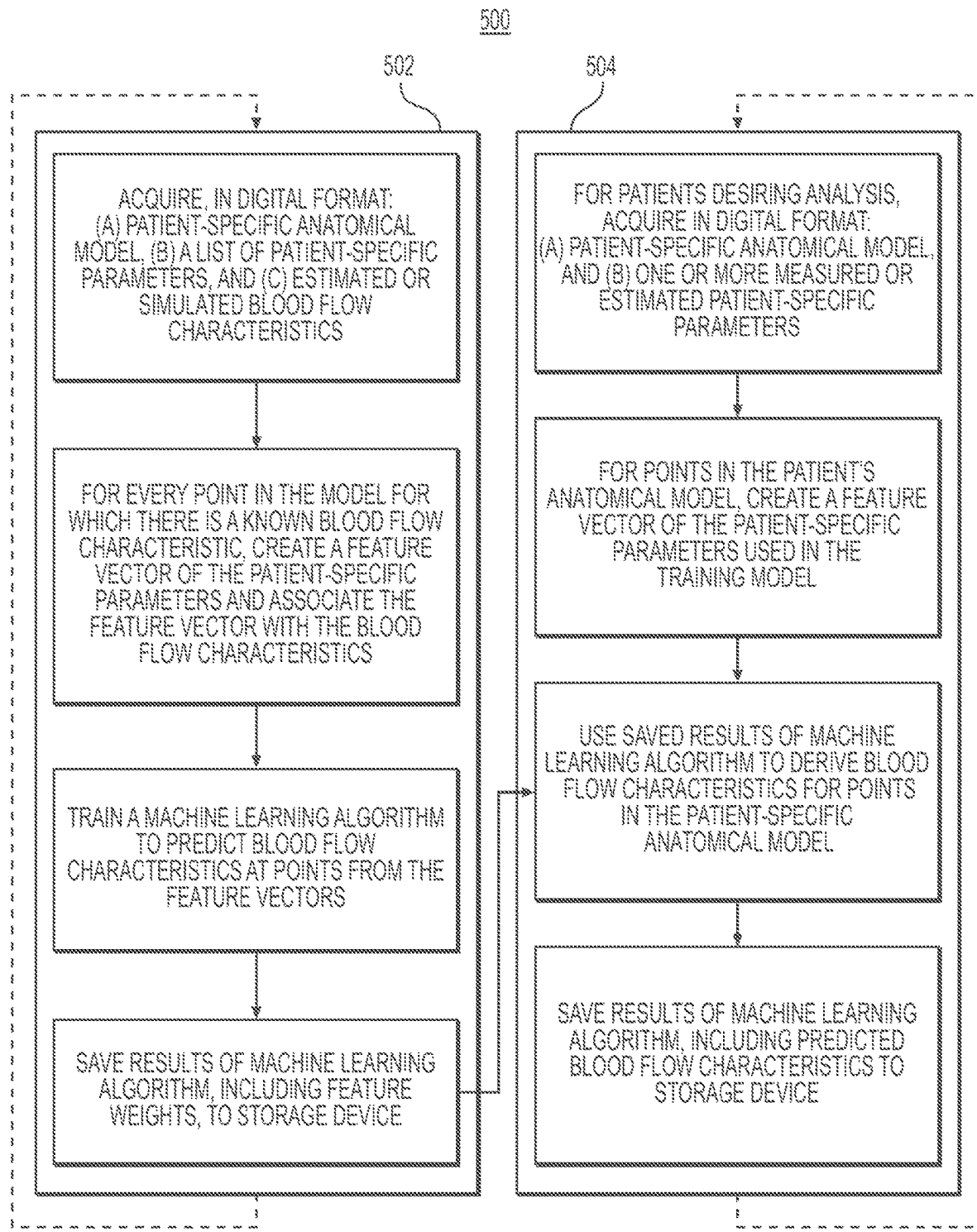
FIG. 5 is a block diagram of an exemplary method 500 for estimating blood flow and/or blood supply demand characteristics on one or more points of a patient-specific vascular and/or anatomical model(s) by executing a machine learning algorithm on one or more patient-specific parameters, according to an exemplary embodiment of the present disclosure.

FIG. 5 is a block diagram of an exemplary method 500 for estimating the blood flow characteristics, and/or blood supply demand characteristics at one or more points of a patient-specific vascular and/or anatomical model using a machine learning algorithm executed on one or more patient-specific parameters, according to an exemplary embodiment of the present disclosure. The patient-specific vascular and/or anatomical model(s) may be of a recipient, a recipient's organ, tissue, and/or vasculature to be replaced, a donor, and/or a donor's organ, tissue, and/or vasculature to be transplanted. In some embodiments, the patient-specific vascular and/or anatomical model may be of the unified model of a recipient or recipient's organ, tissue, and/or vasculature, after a virtual or an actual transplantation. The patient-specific parameters may include characteristics and/or features that may be obtained from a patient or a library of global parameters that may correlate with and/or predict blood flow characteristics and/or blood supply demand characteristics, at least when used in a machine learning algorithm. Thus, the patient-specific parameters may include, but are not limited to, anatomical characteristics (e.g., geometry of organs, tissues, and/or vessels), physiological characteristics (e.g., blood viscosity, pressure, patient activity, etc.), patient biographical characteristics (age, medical history, blood type, etc.), image characteristics (e.g., intensity gradient), and/or characteristics specific to an organ or tissue (e.g., state of an organ).

Method 500 of FIG. 5 may be performed by server systems 106, based on information received from physicians 102 and/or third party providers 104 over electronic network 100. In addition, method 500 of FIG. 5 may include a training method 502, for training one or more machine learning algorithms based on patient-specific parameters from numerous patients and measured, estimated, and/or simulated blood flow and/or blood supply demand characteristics, and a production method 504 for using the machine learning algorithm results to predict the blood flow and/or blood supply demand characteristics of an intended transplant recipient or donor.

In one embodiment, training method 502 may involve acquiring, for each of a plurality of individuals, e.g., in digital format: (a) a patient-specific vascular and/or anatomical model, (b) one or more measured or estimated patient-specific parameters, and (c) estimated or simulated blood flow and/or blood supply demand characteristics. Training method 502 may involve, for one or more points in each patient's model, creating a feature vector of the locational information at one or more points of the vascular and/or anatomical model and one or more patient-specific parameters, and associating the feature vector with the values for blood flow and/or blood supply demand at those points of the vascular and/or anatomical model. Training method 502 may save the results of the machine learning algorithm, including feature weights, in a storage device of server systems 106. The stored feature weights may define the extent to which patient-specific parameters and/or anatomical location are predictive of blood flow and/or blood supply demand characteristics.

In one embodiment, production method 504 may involve estimating blood flow and/or blood supply demand characteristics for a particular patient, based on results of executing training method 502. In one embodiment, production method 504 may include acquiring, e.g. in digital format: (a) a patient-specific vascular and/or anatomical model, and (b) one or more measured or estimated patient-specific parameters. For multiple points in the patient's vascular and/or anatomical model, production method 504 may involve creating a feature vector of the locational information on the model and one or more patient-specific parameters used in the training mode. Production method 504 may use saved results of the machine learning algorithm to produce estimates of the patient's blood flow and/or blood supply demand characteristics for each point in the patient-specific geometric model. Finally, production method 504 may include saving the results of the machine learning algorithm, including predicted blood flow and/or blood supply demand characteristics, to a storage device of server systems 106.

It is contemplated that various steps of method 500 may be used to predict transplantation characteristics other than blood flow characteristics and/or blood supply demand characteristics. In one embodiment, one may use the machine learning techniques presented in method 500 to predict an immunological response in the unified model of a recipient after a virtual or actual transplantation. For example, training method 502 may creating a feature vector of the locational information at one or more points of the vascular and/or anatomical model and one or more patient-specific parameters, and associating the feature vectors with one or more immunological characteristics (e.g. quantities of various lymphocytes), at those points of the vascular and/or anatomical model. In such an embodiment, the patient-specific parameters may include, for example: genetic data; molecular characteristics of cell surfaces of a tissue, organ, and/or vasculature of a donor or recipient; and/or data on antibodies possessed by a recipient or donor. Consequently, production method 504 may include use saved results of the machine learning algorithm to determine immunological characteristics for each point in the patient-specific geometric model, and predict an immune response of a transplantation.

FIG. 6 is a block diagram of exemplary method 600 for assessing the suitability and consequences for an actual organ or tissue transplantation using blood flow characteristics and/or organ-specific or tissue-specific functional characteristics of the connected system, according to an exemplary embodiment of the present disclosure. Furthermore, method 600 may be an exemplary embodiment of performing step 210 of method 200. Method 600 may be performed by server systems 106, based on information, images, and data received from physicians 102 and/or third party providers 104 over electronic network 101.

Step 602 may include receiving or generating a unified model of the connected system of the post-transplantation organ, tissue, and/or vasculature. The model may be a 2D, 3D, and/or 4D (e.g., time resolved volumetric imaging).

Steps 604A, 604B, and 604C may include receiving information related to one or more of the blood flow characteristics, blood supply demand characteristics, and/or functional characteristics of the connected system, original system vasculature of the intended transplant recipient, and/or original organ, tissue, and/or vasculature of the intended transplant donor, respectively.

In one embodiment, as shown in FIG. 6, step 604A may include receiving blood flow characteristics of the original system vasculature of the intended transplant recipient. Step 604B may include receiving blood flow characteristics and functional characteristics of the connected system post transplantation. Step 604C may include receiving blood supply demand characteristics of the original organ, tissue, vasculature of the intended transplant donor.

Step 606 may include determining the likelihood of success for a contemplated transplantation using one or more factors that have been described in steps 608A, 608B, 608C, 608D, 608E, and 608F. The one or more factors may be based on the received blood flow characteristics, blood supply demand characteristics, and/or functional characteristics, and may include patient-specific characteristics. In one embodiment, the likelihood of success is computed as a score based on the one or more factors. For example, the score may be one or more of a probability of success, a quantification of perfusion deficit to the transplanted organ, a quantification of a systemic change to the patient, a categorical assessment (e.g., "excellent", "good", "fair", "poor", etc.), and/or an organ-specific functional assessment (e.g., the capability of the organ to perform its function based on the blood perfusion to that organ). Other suitable means of assessing a potential transplantation success also are contemplated.

Step 608A may include determining whether a blood flow, blood pressure, or perfusion to the organ, tissue, and/or vasculature of the donor meets an expected magnitude. The expected magnitude may be obtained, for example, from a population standard or from a comparable organ, tissue, and/or vasculature of the recipient (e.g., another kidney, limb, etc.).

Step 608B may include determining whether the determined blood flow characteristic(s) may compare unfavorably to the received blood flow characteristic(s) for an intact organ, tissue, and/or vasculature of the donor. Step 608C may include determining whether the received blood flow characteristics for the connected system is similar to the received blood flow characteristic for the original organ, tissue, and/or vasculature of the donor and/or recipient. Step 608D may include determining the functional status of the desired organ or tissue. Step 608E may include determining whether there is a risk or an existence of a large vessel insufficiency (e.g., when a vessel cannot carry sufficient blood flow) in the connected system. In some embodiments, large vessel insufficiency may occur because a vessel is too small in size (e.g., too small in diameter), is diseased (e.g., atherosclerotic plaque or thrombus causing obstruction of the lumen), and/or is injured (e.g., trauma, intimal flap, etc.). Large vessel insufficiency may be based on organ, tissue, and/or vasculature of the donor and/or recipient. Furthermore, large vessel insufficiency may be due to an anastomosis of two blood vessels (producing a stenosis that obstructs blood flow). Likewise, step 608F may include determining whether there is a risk or an existence of threatened or failing organs. Steps 608A, 608B, 608C, 608D, 608E, and 608F may be used in the determination of the likelihood of success for an actual transplantation, in step 606, and may be performed using the unified model of the connected system, and the received blood flow characteristics, blood supply demand characteristics, and/or functional characteristics of the original system vasculature of the intended transplant recipient, the connected system post transplantation, and/or the original organ, tissue, and/or vasculature of the intended transplant donor.

In one embodiment, step 610 may include outputting the result of the determination of the likelihood of success for an actual organ or tissue transplantation to an electronic storage medium and/or display of server systems 106. In one embodiment, the output result may include various transplantation characteristics (e.g., blood flow, blood supply demand, functional characteristics, etc.) that may have been registered and digitally overlaid on the unified model of the connected system. Thus, the model may visually illustrate the likelihood of success based on the registered and digitally overlaid data.

In some embodiments, for example, where a patient receives an actual transplantation, method 700 may be performed subsequent to methods 600.

Figure 7:
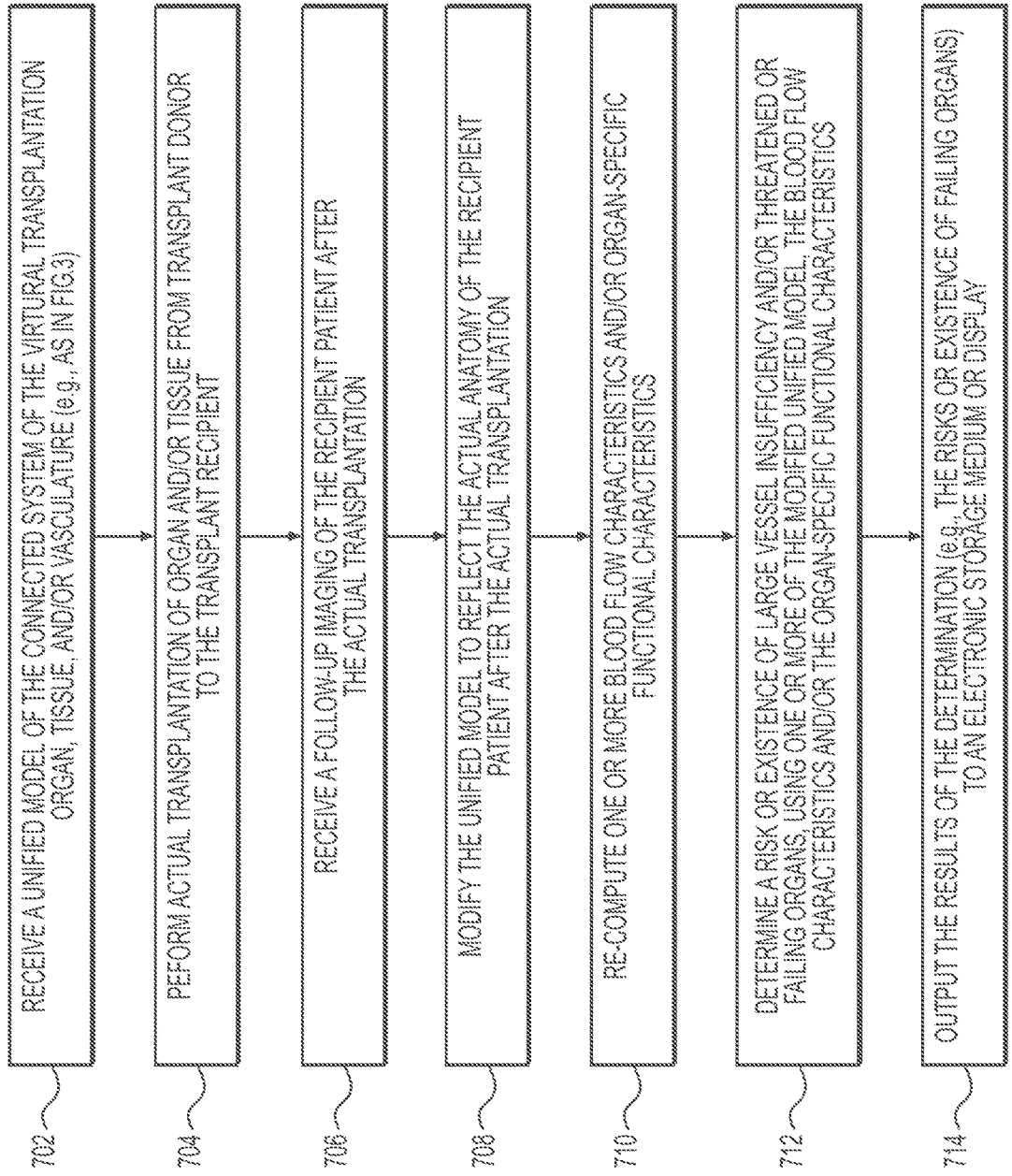
FIG. 7 is a block diagram of exemplary method 700 of determining the risk or existence of large vessel insufficiency and/or threatened or failing organs using blood flow characteristics and/or organ-specific or tissue-specific functional characteristics of the connected system after an actual transplantation, according to an exemplary embodiment of the present disclosure.

FIG. 7 is a block diagram of an exemplary method 700 for determining the risk or existence of large vessel insufficiency and/or threatened or failing organs using blood flow characteristics and/or organ-specific or tissue-specific functional characteristics of the connected system after an actual transplantation. Furthermore, method 700 may be optionally performed subsequent to methods 200, 300, and/or 600, and after an intended transplant recipient patient undergoes an actual transplantation. Method 700 may be performed by server systems 106, based on information, images, and data received from physicians 102 and/or third party providers 104 over electronic network 101.

Step 702 may include receiving a unified model of the connected system of the virtual transplantation organ, tissue, and/or vasculature. The unified model may be generated or received using the steps of method 200 and/or 300. Furthermore, step 704 may include performing an actual transplantation of an organ and/or tissue from the transplant donor to the transplant recipient.

Furthermore, step 706 may include receiving one or more follow-up images of the recipient patient following the actual transplantation. The images may be obtained from any one or more invasive or noninvasive scanning modalities, described above, The one or more received follow-up images may be automatically segmented into one or more voxels, using a computer processor. Step 706 may further include extracting anatomical and physiological information from the received one or more follow-up images of the recipient patient. In some embodiments, the follow-up images may be obtained and/or anatomical and physiological information may be extracted during the transplantation procedure itself.

Step 708 may include modifying the received unified model to reflect the actual anatomy of the recipient patient after the actual transplantation. The modification may be based on the received one or more images and/or anatomical and physiological information extracted from the images. In some embodiments, for example, where the follow up-images are obtained and/or anatomical and physiological information are extracted during the transplantation procedure, the unified model may also be modified during the transplantation procedure, in real time.

Step 710 may include re-computing various transplantation characteristics, including, but not limited to, one or more blood flow characteristics and/or the organ-specific functional characteristics. In some embodiments, for example, immunological characteristics may be re-computed and/or measured during or after the transplantation. These immunological characteristics may include, for example, evidence of and/or quantities of various lymphocytes (e.g., B cells, T cells, etc.). Step 710 may be performed using the received one or more follow-up images or the modified unified model using the techniques presented in method 500 and/or step 312 of method 300. In some embodiments, various transplantation characteristics (e.g., blood flow characteristics, organ-specific functional characteristics, etc.) may be obtained directly during the transplantation procedure, e.g., via catheterization.

Step 712 may include determining a risk or existence of large vessel insufficiency and/or threatened or failing organs, based on the re-computed blood flow characteristics and/or organ-specific functional characteristics. Step 712 may be performed using the techniques discussed for performing method 600 and/or step 210 of method 200. Step 714 may include outputting the results of the determination (e.g., the risks or existence of failing organs) to an electronic storage medium or display. Furthermore, step 714 may include generating a signal indicating the severity of the risk of large vessel insufficiency and/or threatened or failing organs, In some embodiments, step 714 may include estimating the lifespan of the recipient and/or an organ or tissue of the recipient, based on the determined risk or existence of large vessel insufficiency and/or threatened or failing organs. In such embodiments, the estimated lifespan may be outputted to an electronic storage medium or display, for example, so that medical personnel may immediately attend to the patient or perform another transplant.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer implemented method for assessing organ or tissue transplantation, the method comprising:
   receiving one or more pre-transplantation medical images of a transplant recipient;
   identifying voxels of the one or more pre-transplantation medical images of the transplant recipient that belong to a vasculature of the transplant recipient that provides circulation to a recipient organ or a recipient tissue intended to be replaced during a transplant;
   constructing a patient-specific recipient anatomical model of the transplant recipient based on the identified voxels of the vasculature of the transplant recipient;
   receiving one or more pre-transplantation medical images of a donor organ or a donor tissue of a transplant donor;
   identifying voxels of the one or more pre-transplantation medical images of the transplant donor that belong to a vasculature of the transplant donor that provides circulation to the donor organ or the donor tissue intended to be replaced during the transplant;
   constructing a patient-specific recipient anatomical model of the transplant donor based on the identified voxels of the vasculature of the transplant donor;
   estimating blood flow through the patient-specific-recipient anatomical model of the transplant recipient to compute one or more blood flow characteristics of the transplant recipient;
   automatically determining one or more connections between the recipient organ or the recipient tissue intended to be replaced during the transplant and the vasculature of the transplant recipient;
   using the one or more connections, updating the patient-specific recipient anatomical model of the transplant recipient to construct a patient-specific virtual transplant model;
   receiving one or more follow-up medical images of the transplant recipient during a transplantation procedure;
   during the transplantation procedure, automatically segmenting the one or more follow-up medical images and extracting anatomical characteristics from the one or more follow-up medical images;
   in real time, during the transplantation procedure, updating the patient-specific virtual transplant model based on the automatic segmenting of the one or more follow-up medical images and the extracting of the anatomical characteristics from the one or more follow-up medical images;
estimating an updated blood flow through the updated patient-specific virtual transplant model;
evaluating a risk of an insufficient blood flow to the donor tissue or the donor organ transplanted during the transplantation procedure using the updated patient-specific virtual transplant model; and
outputting the evaluation into an electronic storage medium or display.

2. The computer implemented method of claim 1, further comprising:
determining one or more pre-transplantation blood flow characteristics using the patient-specific recipient anatomical model of the transplant recipient; and
evaluating a planned transplantation using a comparison of the computed one or more blood flow characteristics of the transplant recipient and the determined one or more pre-transplantation blood flow characteristics of the transplant recipient.

3. The computer implemented method of claim 1, wherein the updated patient-specific recipient virtual transplant model includes vasculature of the transplant recipient that will supply blood to the donor tissue or the donor organ transplanted during the transplantation procedure.

4. The computer implemented method of claim 1, further comprising:
computing one or more functional characteristics of the recipient organ or the recipient tissue intended to be replaced; and
evaluating a planned transplantation using the computed one or more blood flow characteristics and the one or more functional characteristics.

5. The computer implemented method of claim 1, wherein the risk of insufficient blood flow includes an existence of at least one large vessel insufficiency for supplying blood to the donor tissue or the donor organ transplanted during the transplantation procedure.

6. The computer implemented method of claim 1, wherein the risk of insufficient blood flow further includes a risk of a failure of the donor tissue or the donor organ transplanted during the transplantation procedure.

7. The computer implemented method of claim 1, wherein evaluating the risk of insufficient blood flow further comprises: determining a functional status of the donor tissue or the donor organ transplanted during the transplantation procedure.

8. The computer implemented method of claim 1, wherein evaluating the risk of insufficient blood flow to the donor tissue or the donor organ transplanted during the transplantation procedure includes receiving one or more blood flow characteristics of the vasculature of the intended transplant donor, wherein the donor tissue or the donor organ transplanted during the transplantation procedure originates with the transplant donor.

9. A system for assessing organ or tissue transplantation, the system comprising:
at least one data storage device storing instructions for assessing organ or tissue transplantation; and
at least one processor configured to execute the instructions to perform operations comprising:
receiving one or more pre-transplantation medical images of a transplant recipient;
identifying voxels of the one or more pre-transplantation medical images of the transplant recipient that belong to a vasculature of the transplant recipient that provides circulation to a recipient organ or a recipient tissue intended to be replaced during a transplant;
constructing a patient-specific recipient anatomical model of the transplant recipient based on the identified voxels of the vasculature of the transplant recipient;
receiving one or more pre-transplantation medical images of a donor organ or a donor tissue of a transplant donor;
identifying voxels of the one or more pre-transplantation medical images of the transplant donor that belong to a vasculature of the transplant donor that provides circulation to the donor organ or the donor tissue intended to be replaced during the transplant;
constructing a patient-specific recipient anatomical model of the transplant donor based on the identified voxels of the vasculature of the transplant donor;
estimating blood flow through the patient-specific-recipient anatomical model of the transplant recipient to compute one or more blood flow characteristics of the transplant recipient;
automatically determining one or more connections between the recipient organ or the recipient tissue intended to be replaced during the transplant and the vasculature of the transplant recipient;
using the one or more connections, updating the patient-specific recipient anatomical model of the transplant recipient to construct a patient-specific virtual transplant model;
receiving one or more follow-up medical images of the transplant recipient during a transplantation procedure;
during the transplantation procedure, automatically segmenting the one or more follow-up medical images and extracting anatomical characteristics from the one or more follow-up medical images;
in real time, during the transplantation procedure, updating the patient-specific virtual transplant model based on the automatic segmenting of the one or more follow-up medical images and the extracting of the anatomical characteristics from the one or more follow-up medical images;
estimating an updated blood flow through the updated patient-specific virtual transplant model;
evaluating a risk of an insufficient blood flow to the donor tissue or the donor organ transplanted during the transplantation procedure using the updated patient-specific virtual transplant model; and
outputting the evaluation into an electronic storage medium or display.

10. The system claim 9, the operations further comprising:
determining one or more pre-transplantation blood flow characteristics using the patient-specific recipient anatomical model of the transplant recipient; and
evaluating a planned transplantation using a comparison of the computed one or more blood flow characteristics of the transplant recipient and the determined one or more pre-transplantation blood flow characteristics of the transplant recipient.

11. The system claim 9, wherein the updated patient-specific recipient virtual transplant model includes vasculature of the transplant recipient that will supply blood to the donor tissue or the donor organ transplanted during the transplantation procedure.

12. The system claim 9, wherein the processor is further configured for:
computing one or more functional characteristics of the recipient organ or the recipient tissue intended to be replaced; and evaluating a planned transplantation using the computed one or more blood flow characteristics and the one or more functional characteristics.

13. The system claim 9, wherein the risk of insufficient blood flow further includes a risk of a failure of the donor tissue or the donor organ transplanted during the transplantation procedure.

14. The system of claim 9, wherein evaluating the risk of insufficient blood flow further comprises:
determining a functional status of the donor tissue or the donor organ transplanted during the transplantation procedure.

15. The system of claim 9, wherein the risk of insufficient blood flow includes an existence of at least one large vessel insufficiency for supplying blood to the donor tissue or the donor organ transplanted during the transplantation procedure.

16. The system of claim 9, wherein evaluating the risk of insufficient blood flow to the donor tissue or the donor organ transplanted during the transplantation procedure includes receiving one or more blood flow characteristics of the vasculature of the intended transplant donor, wherein the donor tissue or the donor organ transplanted during the transplantation procedure originates with the transplant donor.

17. A non-transitory computer-readable medium storing instructions that, when executed by a computer, cause the computer to perform operations for assessing organ or tissue transplantation, the operations comprising:
receiving one or more pre-transplantation medical images of a transplant recipient;
identifying voxels of the one or more pre-transplantation medical images of the transplant recipient that belong to a vasculature of the transplant recipient that provides circulation to a recipient organ or a recipient tissue intended to be replaced during a transplant;
constructing a patient-specific recipient anatomical model of the transplant recipient based on the identified voxels of the vasculature of the transplant recipient;
receiving one or more pre-transplantation medical images of a donor organ or a donor tissue of a transplant donor;
identifying voxels of the one or more pre-transplantation medical images of the transplant donor that belong to a vasculature of the transplant donor that provides circulation to the donor organ or the donor tissue intended to be replaced during the transplant;
constructing a patient-specific recipient anatomical model of the transplant donor based on the identified voxels of the vasculature of the transplant donor;
estimating blood flow through the patient-specific-recipient anatomical model of the transplant recipient to compute one or more blood flow characteristics of the transplant recipient;
automatically determining one or more connections between the recipient organ or the recipient tissue intended to be replaced during the transplant and the vasculature of the transplant recipient;
using the one or more connections, updating the patient-specific recipient anatomical model of the transplant recipient to construct a patient-specific virtual transplant model;
receiving one or more follow-up medical images of the transplant recipient during a transplantation procedure;
during the transplantation procedure, automatically segmenting the one or more follow-up medical images and extracting anatomical characteristics from the one or more follow-up medical images;
in real time, during the transplantation procedure, updating the patient-specific virtual transplant model based on the automatic segmenting of the one or more follow-up medical images and the extracting of the anatomical characteristics from the one or more follow-up medical images;
estimating an updated blood flow through the updated patient-specific virtual transplant model;
evaluating a risk of an insufficient blood flow to the donor tissue or the donor organ transplanted during the transplantation procedure using the updated patient-specific virtual transplant model; and
outputting the evaluation into an electronic storage medium or display.

18. The computer-readable medium of claim 17, the operations further comprising:
determining one or more pre-transplantation blood flow characteristics using the patient-specific recipient anatomical model of the transplant recipient; and
evaluating a planned transplantation using a comparison of the computed one or more blood flow characteristics of the transplant recipient and the determined one or more pre-transplantation blood flow characteristics of the transplant recipient.

19. The computer-readable medium of claim 17, the operations further comprising:
computing one or more functional characteristics of the recipient organ or the recipient tissue intended to be replaced; and
evaluating a planned transplantation using the computed one or more blood flow characteristics and the one or more functional characteristics.

20. The computer-readable medium of claim 17, wherein the updated patient-specific recipient virtual transplant model includes vasculature of the transplant recipient that will supply blood to the donor tissue or the donor organ transplanted during the transplantation procedure.

* * * * *

UNITED STATES PATENT AND TRADEMARK OFFICE
CERTIFICATE OF CORRECTION

| | |
|---|---|
| PATENT NO. | : 11,918,293 B2 |
| APPLICATION NO. | : 17/106987 |
| DATED | : March 5, 2024 |
| INVENTOR(S) | : Leo Grady, Charles A. Taylor and Christopher Zarins |

It is certified that error appears in the above-identified patent and that said Letters Patent is hereby corrected as shown below:

In the Specification

In Column 1, Line 13, delete "2016," and insert --2015,--.

In the Claims

In Column 14, Line 47, in Claim 1, replace "patient-specific-recipient" with "patient-specific recipient".

In Column 16, Line 16, in Claim 9, replace "patient-specific-recipient" with "patient-specific recipient".

In Column 16, Line 48, in Claim 10, after "system" insert --of--.

In Column 16, Line 58, in Claim 11, after "system" insert --of--.

In Column 16, Line 63, in Claim 12, after "system" insert --of--.

In Column 17, Line 4, in Claim 13, after "system" insert --of--.

Signed and Sealed this
Twenty-ninth Day of April, 2025

Coke Morgan Stewart
*Acting Director of the United States Patent and Trademark Office*